(12) United States Patent
Aoki et al.

(10) Patent No.: US 8,258,340 B2
(45) Date of Patent: *Sep. 4, 2012

(54) METHOD FOR PRODUCING β-MERCAPTO CARBOXYLIC ACIDS

(75) Inventors: Hidemasa Aoki, Kawasaki (JP); Akio Kuroiwa, Kawasaki (JP); Akira Shibuya, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/921,495

(22) PCT Filed: Mar. 11, 2009

(86) PCT No.: PCT/JP2009/055213
§ 371 (c)(1),
(2), (4) Date: Sep. 8, 2010

(87) PCT Pub. No.: WO2009/113711
PCT Pub. Date: Sep. 17, 2009

(65) Prior Publication Data
US 2011/0015436 A1    Jan. 20, 2011

(30) Foreign Application Priority Data
Mar. 12, 2008  (JP) .................. 2008-062437

(51) Int. Cl.
*C07B 53/00*    (2006.01)
(52) U.S. Cl. .................. 562/606
(58) Field of Classification Search .......... None
See application file for complete search history.

(56) References Cited

U.S. PATENT DOCUMENTS

| | | | | |
|---|---|---|---|---|
| 5,821,382 A | * | 10/1998 | Hino et al. | 560/146 |
| 5,877,349 A | * | 3/1999 | Arretz | 562/606 |
| 6,472,354 B2 | | 10/2002 | Luyendijk et al. | |
| 6,544,936 B2 | | 4/2003 | Devaux | |

FOREIGN PATENT DOCUMENTS

| | | | |
|---|---|---|---|
| EP | 0 825 179 A | | 2/1998 |
| JP | 07-228568 | * | 8/1995 |
| JP | 7-228568 A | | 8/1995 |
| JP | 2001-187778 A | | 7/2001 |
| JP | 2001-354643 A | | 12/2001 |
| JP | 2001-354644 A | | 12/2001 |
| JP | 2003-252918 A | | 9/2003 |

OTHER PUBLICATIONS

Machine Translation of 07-228568.*
Dahlbom, R., "The Addition of Hydrogen Sulphide to Some Unsaturated Aliphatic Nitriles and Carboxylic Acids," Acta Chemica Scandinavica (1951), 5, pp. 690-698.

* cited by examiner

Primary Examiner — Karl J Puttlitz
(74) Attorney, Agent, or Firm — Sughrue Mion, PLLC

(57) ABSTRACT

An object of the present invention is to provide a method for industrially producing β-mercapto carboxylic acids that are useful as synthetic raw materials for medicines and agrochemicals or as additives for polymer compounds from easily available α,β-unsaturated carboxylic acids in high yields and productivity.

The present invention is characterized in that a solvent having an amide group and represented by the formula (1) is used when the α,β-unsaturated carboxylic acids are reacted with hydrogen sulfides to produce the β-mercapto carboxylic acids. Particularly, it is more preferable to carry out the reaction at a pH range of 6.0 to 8.5:

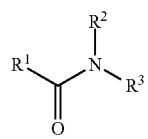

(1)

(In the formula (1), $R^1$ represents any one of a hydrogen atom, an alkoxy group having 1 to 5 carbon atoms, an alkyl group having 1 to 5 carbon atoms, an amino group, and an alkylamino group having 1 to 5 carbon atoms; $R^2$ and $R^3$ each represents independently any one of a hydrogen atom and an alkyl group having 1 to 5 carbon atoms; when both $R^2$ and $R^3$ are not a hydrogen atom, $R^2$ and $R^3$ may together form a ring structure through an alkylene group; and when both $R^1$ and $R^2$ are not a hydrogen atom, $R^1$ and $R^2$ may form a ring structure through an alkylene group).

10 Claims, No Drawings

US 8,258,340 B2

METHOD FOR PRODUCING β-MERCAPTO CARBOXYLIC ACIDS

TECHNICAL FIELD

The present invention relates to a method, wherein any one selected from an α,β-unsaturated carboxylic acid, an α,β-unsaturated carboxylic acid ester, an α,β-unsaturated amide, an α,β-unsaturated aldehyde, and an α,β-unsaturated ketone (hereinafter, these are collectively referred to as the "α,β-unsaturated carboxylic acids") is a raw material compound, and any one of the α,β-unsaturated carboxylic acids is reacted with hydrogen sulfide to efficiently produce any one of a β-mercapto carboxylic acid, a β-mercapto carboxylic acid ester, a β-mercapto amide, a β-mercapto aldehyde, and a β-mercapto ketone (hereafter, these are collectively referred to as the "β-mercapto carboxylic acids"), corresponding to the raw material compound.

BACKGROUND ART

A mercapto compound has heretofore been widely used as synthetic raw materials for various medicines and agrochemicals. Above all, a β-mercapto carbonyl compound is recognized for the usefulness as an antioxidant, and is industrially utilized as a stabilizer for a polymeric compound (see Japanese Patent Laid-Open Publication No. 2003-252918; Patent Document 1).

As one of methods for producing a β-mercapto carbonyl compound, there is a known method in which an α,β-unsaturated carboxylic acid and hydrogen sulfide are subjected to a Michael addition reaction.

Also, it is reported that a Michael addition reaction using acrylic acid as the α,β-unsaturated carboxylic acid proceeds by using hydrogen sulfide in the presence of diethylamine (see Acta Chimica Scandinavica 1951, 5, 690-698; Non-Patent Document 1).

However, in the method using the reaction described in Non-Patent Document 1, the productivity is low because diethylamine is used in large excess and the reaction takes a long time. Therefore, in order to produce a β-mercapto carbonyl compound industrially and efficiently, there remains a problem that recovery equipment for diethylamine is necessary.

Further, it is reported that β-mercaptopropionic acid can be synthesized by reacting acrylic acid with sodium hydrosulfide in the presence of a large excess of sodium hydroxide (see Japanese Patent Laid-Open Publication No. 2001-187778; Patent Document 2).

In this method, however, 5 or more equivalents of sodium hydroxide relative to the substrate are needed in order to suppress a side reaction, and the excess alkali is needed to be neutralized with an acid. Therefore, a large amount of the inorganic salt generated is required to be disposed of, and there has been a problem that this method is not suitable for the industrial production.

Further, Japanese Patent Laid-Open Publication No. 2001-354643 (Patent Document 3) and Japanese Patent Laid-Open Publication No. 2001-354644 (Patent Document 4) disclose a method for producing sulfurized olefins in which olefins are sulfurized by using sulfur derivatives and hydrogen sulfide in the presence of a solid acid catalyst such as zeolite and the like.

In Patent Documents 3 and 4, there are descriptions about the generation of mercaptan as an intermediate. However, in these documents, the final target compound is not the mercapto compound which is the objective compound of the present invention, but organic sulfides, disulfides, and polysulfide. Therefore, the generation of the mercaptan corresponding to the mercapto compound is suppressed as low a level as possible.

Further, Patent Documents 3 and 4 describe that the raw material olefins may be diluted with a solvent but the solvents described therein are saturated aliphatic hydrocarbons such as methane, ethane, pentane, and the like, namely non-polar solvents. There is no description, and no suggestion about using a polar solvent which is compatible with a polar solvent such as water and the like. Further, there is no description about the effect thereof.

[Patent Document 1] Japanese Patent Laid-Open Publication No. 2003-252918
[Patent Document 2] Japanese Patent Laid-Open Publication No. 2001-187778
[Patent Document 3] Japanese Patent Laid-Open Publication No. 2001-354643
[Patent Document 4] Japanese Patent Laid-Open Publication No. 2001-354644
[Non-Patent Document 1] Acta Chimica Scandinavica 1951, 5, 690-698

DISCLOSURE OF THE INVENTION

Problems to be Solved by the Invention

An object of the present invention is to provide a method for industrially producing β-mercapto carboxylic acids that are useful as a synthetic raw material for medicines and agrochemicals or as an additive for polymer compounds, in high yield and in high productivity, using easily available α,β-unsaturated carboxylic acids as a raw material.

Means to Solve the Problem

The present inventors conducted diligent research and, as a result, have found a method in which a solvent containing an amide group or a solvent in which hydrogen of an amide group is replaced with an alkyl group is used as a reaction solvent when α,β-unsaturated carboxylic acids react with hydrogen sulfide to produce β-mercapto carboxylic acids. Further, in the method, the inventors have found especially a method in which the reaction is carried out at a specific hydrogen ion concentration (a specific pH range). The present invention has thus been achieved, based on these findings.

That is, the present invention relates to a method for producing the β-mercapto carboxylic acids as described in the following [1] to [10].

[1] A method for producing β-mercapto carboxylic acids, comprising:
preparing a liquid comprising any one of α,β-unsaturated carboxylic acids selected from an α,β-unsaturated carboxylic acid, an α,β-unsaturated carboxylic acid ester, an α,β-unsaturated amide, an α,β-unsaturated aldehyde, and α,β-unsaturated ketones, hydrogen sulfides, and a solvent; and then
heating the liquid to react the any one of the α,β-unsaturated carboxylic acids with the hydrogen sulfide, thereby producing any one of β-mercapto carboxylic acids which is selected from β-mercapto carboxylic acid, β-mercapto carboxylic acid ester, β-mercapto amide, β-mercapto aldehyde, and β-mercapto ketone, and corresponds to the α,β-unsaturated carboxylic acids used,
wherein the solvent is selected from a compound represented by the formula (1), and a mixed solvent comprising the compound represented by the formula (1) and water;

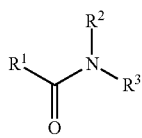

(1)

(In the formula (1), $R^1$ represents any one of a hydrogen atom, an alkoxy group having 1 to 5 carbon atoms, an alkyl group having 1 to 5 carbon atoms, an amino group, and an alkylamino group having 1 to 5 carbon atoms; $R^2$ and $R^3$ each represents independently any one of a hydrogen atom and an alkyl group having 1 to 5 carbon atoms; when both $R^2$ and $R^3$ are not a hydrogen atom, $R^2$ and $R^3$ may together form a ring structure through an alkylene group; and when both $R^1$ and $R^2$ are not a hydrogen atom, $R^1$ and $R^2$ may form a ring structure through an alkylene group).

[2] The method for producing β-mercapto carboxylic acids according to [1], wherein the pH of the liquid measured at 6° C. before the reaction is in the range of 6.0 to 8.5.

[3] The method for producing β-mercapto carboxylic acids according to [1] or [2], wherein the reaction is carried out at the range of 70 to 200° C.

[4] The method for producing β-mercapto carboxylic acids according to [3], wherein the amount of water contained in the mixed solvent is 1 to 50% by mass.

[5] The method for producing β-mercapto carboxylic acids according to any one of [1] to [4], wherein the compound represented by the formula (1) is one or more kinds selected from N-methylformamide (MFA), N,N-dimethylformamide (DMF), N-ethylformamide (EFA), N,N-diethylformamide (DEF), N,N-dimethylacetamide (DMA), 1,3-dimethyl-2-imidazolidinone (DMI), and N-methyl-2-pyrrolidone (NMP).

[6] The method for producing β-mercapto carboxylic acids according to [2], wherein the pH of the liquid is adjusted by a pH adjuster selected from a basic material containing an alkali metal or an alkaline earth metal, and an organic basic material.

[7] The method for producing β-mercapto carboxylic acids according to [1], wherein the α,β-unsaturated carboxylic acids is an α,β-unsaturated carboxylic acid or an α,β-unsaturated carboxylic acid ester.

[8] The method for producing β-mercapto carboxylic acids according to [1] or [7], wherein the α,β-unsaturated carboxylic acid is any one of acrylic acid, methacrylic acid, crotonic acid, 2-pentenoic acid, cinnamic acid, 2-methylcinnamic acid, 3-methycinnamic acid, 4-methylcinnamic acid, 2,3-dimethylcinnamic acid, 2,4-dimethylcinnamic acid, 3,4-dimethylcinnamic acid, 2-hydroxycinnamic acid, 3-hydroxycinnamic acid, 4-hydroxycinnamic acid, 2,3-dihydrocinnamic acid, 2,4-dihydrocinnamic acid, 3,4-dihydrocinnamic acid, 2-hexenoic acid, and 4-methyl-2-pentenoic acid.

[9] The method for producing β-mercapto carboxylic acids according to [1] or [7], wherein the α,β-unsaturated carboxylic acid ester is any one of methyl acrylate, ethyl acrylate, propyl acrylate, butyl acrylate, methyl methacrylate, ethyl methacrylate, propyl methacrylate, butyl methacrylate, methyl crotonate, ethyl crotonate, propyl crotonate, butyl crotonate, methyl 2-pentenoate, ethyl 2-pentenoate, propyl 2-pentenoate, and butyl 2-pentenoate.

[10] The method for producing β-mercapto carboxylic acids according to [1], wherein the α,β-unsaturated ketone is any one of cyclopentenone, cyclohexenone, and cycloheptenone.

EFFECT OF THE INVENTION

According to the production method of the present invention, the β-mercapto carboxylic acids are produced in high yield and in high productivity without necessarily using a solid catalyst and the like. Further, because the β-mercapto carboxylic acids are produced in high yield, the purification process may be simplified and the method of the present invention is extremely useful as an industrial production method.

BEST MODE FOR CARRYING OUT THE INVENTION

Hereinafter, the present invention will be described in detail.
[Reaction]
The reaction used in the present invention yields β-mercapto carboxylic acids, in which an α carbon next to the carbonyl (C=O) carbon and the adjacent β carbon are bonded by a single bond, by reacting α,β-unsaturated carboxylic acids with hydrogen sulfide using a solvent represented by the following formula (1):

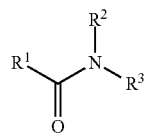

(1)

(In the formula (1), $R^1$ represents any one of a hydrogen atom, an alkoxy group having 1 to 5 carbon atoms, an alkyl group having 1 to 5 carbon atoms, an amino group, and an alkylamino group having 1 to 5 carbon atoms; $R^2$ and $R^3$ each represents independently any one of a hydrogen atom and an alkyl group having 1 to 5 carbon atoms; when both $R^2$ and $R^3$ are not a hydrogen atom, $R^2$ and $R^3$ may together form a ring structure through an alkylene group; and when both $R^1$ and $R^2$ are not a hydrogen atom, $R^1$ and $R^2$ may form a ring structure through an alkylene group).

Further, as an example of the reaction as described above, a reaction of crotonic acid and hydrogen sulfide is shown below.

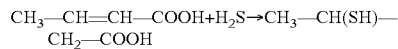

[α,β-Unsaturated Carboxylic Acids]

In the method of the present invention, the α,β-unsaturated carboxylic acids used as a raw material compound may be any one of an α,β-unsaturated carboxylic acid, an α,β-unsaturated carboxylic acid ester, an α,β-unsaturated amide, an α,β-unsaturated aldehyde, and an α,β-unsaturated ketone.

Here, the term, α,β-unsaturated means that an α carbon next to the carbonyl (C=O) carbon and the adjacent β carbon are bonded by a double bond.

The α and β carbons each may be independently bonded with an alkyl group, a cycloalkyl group, an aryl group, an aralkyl group, an alkoxy group, a carboxyl group, an acyl group, an alkoxycarbonyl group (ester), and an acyloxy group instead of a hydrogen atom.

These substituents may be the same or different. In addition, other functional groups may be bonded to these substituents, and may be, for example, an alkyl group having an oxo group (2-oxo-propyl group and the like).

Further, examples of the α,β-unsaturated carboxylic acids used in the present invention also include a compound in which a carboxyl group is bonded to the β carbon of the α,β-unsaturated carboxylic acid, for example, maleic acid, fumaric acid, maleic anhydride and the like.

Further, the α carbon and β carbon may form a cyclic structure through an alkylene group and the like. This cyclic structure may contain a carbonyl carbon (for example, a cyclic ketone and the like) or nitrogen (for example, a lactam and the like).

Among the substituents bonded to the α or β carbon, an alkyl group and an aryl group are preferable from the viewpoint of easy availability of the raw material.

The alkyl groups include a methyl group, an ethyl group, an n-propyl group, an isopropyl group, an n-butyl group, an isobutyl group, a 1-methylpropyl group, a tert-butyl group, an n-pentyl group, an isopentyl group, a 1-methylbutyl group, a 2-methylbutyl group, a 1-ethylpropyl group, an n-hexyl group, an isohexyl group, a 1-methylpentyl group, a 2-methylpentyl group, a 3-methylpentyl group, a 1-ethylbutyl group, and a 2-ethylbutyl group. Among these, a methyl group, an ethyl group, and an isopropyl group are preferable.

The cycloalkyl groups include a cyclopentyl group, a cyclohexyl group, and a cycloheptyl group. Among these, a cyclopentyl group and a cyclohexyl group are preferable from the viewpoint of easy availability of the raw material.

The aryl groups include a phenyl group, a tolyl group, a xylyl group, and a naphthyl group.

The aralkyl groups include a benzyl group, and a phenethyl group. Among these, a benzyl group and a phenethyl group are preferable from the viewpoint of easy availability of the raw material.

The alkoxy groups include a methoxy group and an ethoxy group.

The acyl groups include a formyl group, an acetyl group, and a benzoyl group.

The alkoxycarbonyl groups include a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, an n-pentyloxycarbonyl group, an isopentyloxycarbonyl group, a hexyloxycarbonyl group, an isohexyloxycarbonyl group, a cyclohexyloxycarbonyl group, and a benzyloxycarbonyl group. Among these, a methoxycarbonyl group and an ethoxycarbonyl group are preferable from the viewpoint of easy availability of the raw material.

The acyloxy groups include an acetoxy group and a benzoyloxy group.

In the method of the present invention, the α,β-unsaturated carboxylic acids used as the raw material compound include an α,β-unsaturated carboxylic acid, an α,β-unsaturated carboxylic acid ester, an α,β-unsaturated amide, an α,β-unsaturated aldehyde, and an α,β-unsaturated ketone.

According to the present invention, the β-mercapto carboxylic acids may be industrially produced in higher yield and in higher productivity, particularly when the α,β-unsaturated carboxylic acid and the α,β-unsaturated carboxylic acid ester are used as the raw material.

The reason for this is not clear but it is presumed that when the α,β-unsaturated carboxylic acid or the α,β-unsaturated carboxylic acid ester is used under the production conditions as described in the present specification, the carbonyl group is activated, and thereby the reactivity of the double bond portion is increased.

In addition, in order to produce the desired β-mercapto carboxylic acids, the α,β-unsaturated carboxylic acids corresponding to the β-mercapto carboxylic acids are selected as the raw material compound.

For example, when the β-mercapto carboxylic acid is produced, the α,β-unsaturated carboxylic acid may only be selected as the raw material compound.

Specific examples of the α,β-unsaturated carboxylic acid include acrylic acid, methacrylic acid, crotonic acid, 2-methylcrotonic acid, 3-methylcrotonic acid, 2-pentenoic acid, 2-hexenoic acid, fumaric acid, maleic acid, cinnamic acid, allocinnamic acid, α-methylcinnamic acid, 2-methylcinnamic acid, 3-methylcinnamic acid, 4-methylcinnamic acid, 2,3-dimethylcinnamic acid, 2,4-dimethylcinnamic acid, 3,4-dimethylcinnamic acid, 2-hydroxycinnamic acid, 3-hydroxycinnamic acid, 4-hydroxycinnamic acid, 2,3-dihydrocinnamic acid, 2,4-dihydrocinnamic acid, 3,4-dihydrocinnamic acid, 4-methyl-2-pentenoic acid, 1-cyclohexene carboxylic acid, 1-cyclopentene carboxylic acid, 3-(2-furyl) acrylic acid, 2, 5-dihydrothiophene-3-carboxylic acid, and the like.

Among these, acrylic acid, methacrylic acid, crotonic acid, 2-pentenoic acid, fumaric acid, maleic acid, cinnamic acid, and 4-methyl-2-pentenoic acid are preferable from the viewpoint of easy availability of the raw material.

Specific examples of the α,β-unsaturated carboxylic acid ester include methyl acrylate, ethyl acrylate, propyl acrylate, isopropyl acrylate, butyl acrylate, methyl methacrylate, ethyl methacrylate, propyl methacrylate, isopropyl methacrylate, butyl methacrylate, methyl crotonate, ethyl crotonate, propyl crotonate, isopropyl crotonate, butyl crotonate, methyl 2-pentenoate, ethyl 2-pentenoate, propyl 2-pentenoate, isopropyl 2-pentenoate, butyl 2-pentenoate, dimethyl fumarate, diethyl fumarate, methyl fumarate, ethyl fumarate, dipropyl fumarate, diisopropyl fumarate, dibutyl fumarate, dimethyl maleate, diethyl maleate, methyl maleate, ethyl maleate, dipropylmaleate, diisopropyl maleate, dibutyl maleate, methyl cinnamate, ethyl cinnamate, propyl cinnamate, isopropyl cinnamate, butyl cinnamate, methyl allocinnamate, ethyl allocinnamate, methyl 4-methyl-2-pentenoate, ethyl 4-methyl-2-pentenoate, propyl 4-methyl-2-pentenoate, isopropyl 4-methyl-2-pentenoate, butyl 4-methyl-2-pentenoate, methyl 2,5-dihydrothiophene-3-carboxylate, and the like.

Among these, methyl acrylate, methyl methacrylate, methyl crotonate, ethyl crotonate, methyl 2-pentenoate, ethyl 2-pentenoate, methyl 4-methyl-2-pentenoate, methyl cinnamate, and ethyl cinnamate are more preferable from the viewpoint of easy availability of the raw material.

Specific examples of the α,β-unsaturated amide include acrylamide, N-methylacrylamide, N-ethylacrylamide, methacrylamide, N-methylmethacrylamide, N-ethylmethacrylamide, crotonic acid amide, N-methylcrotonic acid amide, N-ethylcrotonic acid amide, 3-methylcrotonic acid amide, maleic acid amide, cinnamic acid amide, N-methylcinnamic acid amide, N-ethylcinnamic acid amide, α-methylcinnamic acid amide, N-methyl-α-methylcinnamic acid amide, N-ethyl-α-methylcinnamic acid amide, and the like.

Among these, acrylamide, methacrylamide, N-methylmethacrylamide, crotonic acid amide, 3-methylcrotonic acid amide, cinnamic acid amide are more preferable from the viewpoint of easy availability of the raw material.

Specific examples of the α,β-unsaturated aldehyde include acrolein, crotonic aldehyde, 3-methylcrotonic aldehyde, 2-pentene aldehyde, fumaric aldehyde, maleic aldehyde, cinnamic aldehyde, α-methylcinnamic aldehyde, 2-methylcinnamic aldehyde, 3-methylcinnamic aldehyde, 4-methylcinnamic aldehyde, 2-hydroxycinnamic aldehyde, 3-hydroxycinnamic aldehyde, 4-hydroxycinnamic aldehyde, and the like.

Among these, crotonic aldehyde, 3-methylcrotonic aldehyde, 2-pentene aldehyde, and cinnamic aldehyde are more preferable from the viewpoint of easy availability of the raw material.

Specific examples of the α,β-unsaturated ketone include methyl vinyl ketone, ethyl vinyl ketone, 3-penten-2-one, 4-phenyl-3-penten-2-one, 3-hexen-2-one, 4-hexen-3-one, 1,3-diphenyl-2-propenone, 4-methyl-3-penten-2-one, cyclopenten-2-one (=cyclopentenone), cyclohexen-2-one (=cyclohexenone), cyclohepten-2-one (=cycloheptenone), carvone, 2(5H)-furanone, 3-methyl-2(5H)-furanone, 4-methyl-2(5H)-furanone, 3,5-dimethyl-2(5H)-furanone, 5,6-dihydro-2H-pyran-2-one, α-methylene-γ-butyrolactone, 3-methyl-2-cyclohexen-1-one, and the like.

Among these, methyl vinyl ketone, ethyl vinyl ketone, cyclopentenone, cyclohexenone, and cycloheptenone are more preferable from the viewpoint of easy availability of the raw material.

[β-Mercapto Carboxylic Acids]

The β-mercapto carboxylic acids obtained according to the present invention are the ones in which a hydrogen atom and a mercapto group are bonded to the α position and β position of the α,β-unsaturated carboxylic acids, respectively.

As described above, in order to obtain the desired β-mercapto carboxylic acids, the α,β-unsaturated carboxylic acids corresponding to the β-mercapto carboxylic acids may only be selected as the raw material compound.

Preferable β-mercapto carboxylic acids include the compound in which a mercapto group (—SH) is bonded to the β position of the preferable α,β-unsaturated carboxylic acids as described above and in which an α carbon next to the carbonyl (C=O) carbon and the adjacent β carbon are bonded by a single bond.

[Hydrogen Sulfide]

Hydrogen sulfide used in the method of the present invention may be hydrogen sulfide gas derived from petroleum refining or synthetic hydrogen sulfide obtained by hydrogenation of sulfur.

Hydrogen sulfide may be fed into a reactor in a gaseous state or may be fed after dissolved in a solvent to be used for the reaction.

When the hydrogen sulfide is fed in a gaseous state, the hydrogen sulfide gas may be pressurized and fed into a space on the reaction liquid or into the reaction liquid through a gas disperser.

When hydrogen sulfide is fed after dissolved in a solvent, the hydrogen sulfide is fed into a mixer for dissolving the hydrogen sulfide in the solvent, to be dissolved in the reaction liquid.

Further, in order to improve handling efficiency, hydrogen sulfide gas may be generated in the reaction liquid.

That is, hydrogen sulfide gas may be supplied to the reaction liquid, by neutralizing sulfides or hydrosulfides such as sodium sulfide, sodium hydrosulfide, ammonium sulfide, and the like in the reaction liquid to generate hydrogen sulfide gas.

The amount of hydrogen sulfide used is preferably 0.7 to 7 moles, more preferably 1.0 to 5 moles, and most preferably 1.1 to 4 moles, relative to 1 mole of C—C double bond of the α,β-unsaturated carboxylic acids.

When the number of moles of the hydrogen sulfide is smaller than 0.7, a sulfide compound which is the byproduct becomes the major product and this is not preferable. When the number of moles of the hydrogen sulfide is larger than 7, there is no decrease in the yields of the β-mercapto carboxylic acids but an apparatus for recovering unreacted hydrogen sulfide becomes large and such a large apparatus is not practical.

When hydrogen sulfide gas is kept dissolved in a solvent prior to the reaction, hydrogen sulfide gas is preferably fed to and kept dissolved in the reaction liquid while maintaining the temperature of the reaction liquid at 10° C. or lower.

[Solvent]

The solvent used in the reaction of the present invention is a compound with the structure shown by the formula (1):

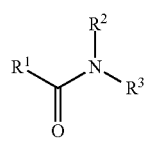

(1)

(In the formula (1), $R^1$ represents any one of a hydrogen atom, an alkoxy group having 1 to 5 carbon atoms, an alkyl group having 1 to 5 carbon atoms, an amino group, and an alkylamino group having 1 to 5 carbon atoms; $R^2$ and $R^3$ each represents independently any one of a hydrogen atom and an alkyl group having 1 to 5 carbon atoms; when $R^2$ and $R^3$ each is not a hydrogen atom, $R^2$ and $R^3$ may together form a ring structure through an alkylene group; further, when $R^1$ and $R^2$ each is not a hydrogen atom, $R^1$ and $R^2$ may form a ring structure through an alkylene group).

The solvents as described above include a solvent having, in the molecule, one or more kinds of the groups selected from an amide group or a group in which a hydrogen(s) of an amide group is (are) replaced with an alkyl group(s) (hereinafter, these are collectively referred to simply as an amide group), a urea group, and a urethane group.

The solvents may be used singly or as a mixture of two or more kinds, or may contain water.

The solvent may be selected by taking into consideration of the solubility and reactivity of hydrogen sulfide and α,β-unsaturated carboxylic acids to be used as the raw material compound, without any limitation on the kind of the solvent.

The solvents with the structure as shown in the formula (1) also include a solvent having a cyclic structure, in addition to a solvent having a linear structure.

The solvent is preferably a solvent in a liquid state at room temperature. However, a compound which is crystallized at room temperature may be used as a solvent when it is used as a mixture with a solvent having one or more groups selected from an amide group, urea group, and urethane group in the molecule, which is in a liquid state at room temperature, or when it is used after dissolving in water.

The solvents whose $R^2$ and $R^3$ together form a ring structure through an alkylene group include N-acetylmorpholine, N-acetylpiperidine, N-acetylpyrrolidine, and N-acetylpiperazine.

Further, the solvents whose $R^1$ and $R^2$ form a ring structure through an alkylene group include N-methyl-2-pyrrolidone (NMP), N-ethyl-2-pyrrolidone, N-butyl-2-pyrrolidone, and N-acetyl-2-pyrrolidone.

Preferable solvents which may be used in a reaction of the present invention include the following.

Specific examples thereof include N,N-dimethylformamide (DMF), N-methyl-2-pyrrolidone (NMP), 1-ethyl-2-pyrrolidinone, 1-methyl-2-piperidone, 1-butyl-2-pyrrolidinone, 1-ethyl-2-piperidone, 1,3-dimethylpiperidone, 1,3-dimethyl-3,4,5,6-tetrahydro-2(1H)-pyrimidinone, 1,3- dimethyl-2-imidazolidinone (DMI), 1,3-diethyl-2-imidazolidinone, 2-pyrrolidinone, γ-butyrolactam, formamide, N-methylformamide, N-ethylformamide, acetamide, N-methylacetamide, N-ethylacetamide, N,N-dimethylacetamide, N,N-diethylacetamide, N-methylpropanamide, and N-ethylpropanamide.

Among these solvents, N,N-dimethylformamide (DMF), 1,3-dimethyl-2-imidazolidinone (DMI), and N-methyl-2-pyrrolidone (NMP) are particularly preferable, from the viewpoint that the β-mercapto carboxylic acids can be industrially produced in higher yield and in higher productivity.

As described above, according to the method of the present invention, these solvents may contain water.

When the solvent contains water, the content of water in the solvent is preferably 1 to 50% by mass, more preferably 1 to 30% by mass, and most preferably 10 to 20% by mass.

The solvent is used preferably in a proportion of 200 to 3500 parts by mass, more preferably 300 to 2000 parts by mass, and most preferably 400 to 1500 parts by mass, relative to 100 parts by mass of the α,β-unsaturated carboxylic acids.

When the amount of the solvent used is less than 200 parts by mass, a side reaction easily proceeds, and in that case, there is a risk that the yield of the β-mercapto unsaturated carboxylic acids is lowered.

When the amount of the solvent used exceeds 3500 parts by mass, the side reaction is suppressed and the yield of the β-mercapto unsaturated carboxylic acids increases. However, because the concentration of the reaction liquid is diluted, the productivity decreases. Therefore, the amount of the solvent used is preferably determined by considering a balance between the reaction yield and the productivity.

[Hydrogen Ion Concentration]

In the reaction used in the present invention, the hydrogen ion concentration of the reaction liquid (pH of the reaction liquid) is important.

The pH before the reaction is measured when the temperature of the reaction liquid containing all raw material compounds is adjusted to 6° C. in order to prevent the hydrogen sulfide contained in the reaction liquid from gasifying.

The pH after the reaction is measured after the reaction liquid is left at 25° C. with the reaction vessel open long enough until the excess hydrogen sulfide gas evaporates and the reaction liquid is in a saturated state.

The pH's before and after the reaction each is preferably in a range of 6.0 to 8.5, more preferably each in a range of 6.5 to 8.0.

When the pH's before and after the reaction is in a range of 6.0 to 8.5, the adjustment of the pH is not particularly needed. However, when the pH is outside the range, it is more preferable to adjust the pH using a pH adjuster so that the pH falls in the range.

When the pH of the reaction liquid after the addition of all raw materials is lower than 6.0, it is preferable to adjust the pH using a basic substance containing an alkali metal or an alkaline earth metal, or an organic base, as the pH adjuster.

When the pH is higher than 8.5, it is preferable to adjust the pH using a mineral acid or an organic acid represented by a lower carboxylic acid and the like.

When the pH is lower than 6.0, the reaction proceeds slowly and, when the pH is higher than 8.5, a side reaction proceed rapidly. In either case, the yield of the desired compound is lowered.

Even though the reason for this is not clear, when the pH of the reaction liquid is lower than 6.0, the reason is presumed as follows. The acid dissociation constant (pKa) of the reaction liquid corresponding to the pH is smaller than the pKa of hydrogen sulfide, therefore, the generation of hydrosulfides anion ($HS^-$) which is an active species becomes less, and the yield is lowered.

When the pH of the reaction liquid exceeds 8.5, the reason is presumed as follows. The pKa of the reaction liquid corresponding to the pH become higher than the pKa's of both the hydrosulfides anion derived from hydrogen sulfide and the hydrosulfides anion derived from the β-mercapto carboxylic acids which is the product. Therefore, each anion reacts with the α,β-unsaturated carboxylic acids which are the raw material compound to decrease the amount of α,β-unsaturated carboxylic acids which are to react with hydrogen sulfide, and the yield is lowered.

[pH Adjuster]

When a basic material is used as the pH adjuster, examples of the basic materials include a basic material containing an alkali metal or an alkaline earth metal (hereinafter, these are also referred to as the "metal-containing basic material"), an organic basic material, and the like. When an acidic material is used, examples of the acidic materials include a mineral acid, a lower carboxylic acid, and the like.

Preferable alkali metals contained in the metal-containing basic materials include lithium, sodium, and potassium. Preferable alkaline earth metals contained in the metal-containing basic materials include magnesium and calcium. These metals may be used singly or as a mixture of two or more kinds.

The alkali metal or the alkaline earth metal is available as a hydroxide, an oxide, an organic metal, an alkoxide compound, a nitrate, a sulfate, a cyanide, a sulfide, or a hydrogen sulfide, and any of them can be used.

Among these, anyone of a hydroxide, an oxide, an organic metal, an alkoxide compound, a sulfide, and a hydrogen sulfide is preferably used.

As the organic basic material, in general, amines can be used. The amines include ammonia, ethylamine, propylamine, dimethylamine, diethylamine, diisopropylamine, dipropylamine, trimethylamine, triethylamine, pyridine, and morpholine. Preferably dimethylamine, diethylamine, triethylamine, and pyridine are used.

The mineral acids include a sulfuric acid, a hydrochloric acid, a nitric acid, and the like. The lower carboxylic acids include a formic acid, an acetic acid, and the like.

In the case that the pH is in the specified range when the α,β-unsaturated carboxylic acid and the amide-based solvent, namely the solvent containing an amide group or a solvent in which hydrogen of an amide group is replaced with an alkyl group as described above, are mixed, the reaction may be carried out with the pH as it is. In that case, the reaction proceeds without containing any pH adjusters.

On the other hand, when the pH adjuster is contained in a catalytic amount, the reaction accelerates. Therefore, a small amount of the pH adjuster is preferably added.

The amount of the pH adjuster added is usually 0.01 to 0.3 equivalent relative to 1 mole of α,β-unsaturated carboxylic acids that are raw materials and, in this range, the reaction proceeds rapidly.

The reason for this is not clear, however it is presumed that the metals or organic bases as the pH adjuster act to accelerate the formation of the hydrosulfides anion, and the reactivity is higher compared to the case where only solvent is added.

[Reaction Concentration]

The concentration of the α,β-unsaturated carboxylic acids in the reaction liquid is preferably 3 to 35% by mass, more preferably 5 to 30% by mass, and most preferably 7 to 20% by mass.

In a reaction concentration of less than 3% by mass, the reaction proceeds very slowly, and in a reaction concentration of more than 35% by mass, the yield is lowered because of a side reaction.

[Reaction Temperature]

The reaction temperature is preferably 70 to 200° C., more preferably 90 to 150° C., and most preferably 95 to 120° C.

At a temperature lower than 70° C., the reaction proceeds slowly and at a temperature higher than 200° C., the yield is lowered in some cases because of a side reaction.

Because volatile gas is generated by heating, a closed system reactor is preferably used in order to prevent the organic solvent and hydrogen sulfide gas from leaking to outside.

Even though the reason is not clear, when the reaction temperature is lower than 70° C., it is presumed that surpassing the activation energy of the reaction is difficult and, as a result, the reaction does not proceed efficiently.

When the reaction temperature is higher than 200° C., it is presumed as follows. Activation energies of both the addition reaction of hydrogen sulfide to the α,β-unsaturated carboxylic acids and the addition reaction of the β-mercapto carboxylic acids, which is generated by the reaction, to the α,β-unsaturated carboxylic acids are surpassed. Therefore, both reactions proceed concurrently, as a result, become competitive reactions, and the yield is lowered.

[Reaction Time]

The reaction time may be controlled in a range of 0.1 to 12 hours. The reaction is generally completed in 2 to 8 hours.

For example, in a reaction using crotonic acid as the raw material compound, the conversion of the raw material becomes 95% or more usually in about 4 hours.

The end point of the reaction may be judged by analyses of the conversion of the raw material compound or the concentration of the β-mercapto carboxylic acids in the reaction liquid by, for example, high performance liquid chromatography (HPLC), gas chromatography (GC), and the like.

[Reaction Pressure]

The reaction pressure is preferably 0.1 to 3 MPa, more preferably 0.2 to 2 MPa, and most preferably 0.4 to 1.5 MPa.

At a pressure less than 0.1 MPa, the reaction proceeds slowly. A pressure more than 3 MPa is not preferable in terms of reaction apparatus management as well as safety.

[Purification]

There is no particular limitation on the method for purifying (isolating) the β-mercapto carboxylic acids from the reaction system after the reaction. However, a purification method whereby the reaction liquid is directly distilled or a purification method by recrystallization is preferable from the viewpoints of process shortening and control of a waste liquid generated from the reaction liquid.

For example, there may be employed a method in which, after removing solid components insoluble in the solvent by filtration, the whole reaction mixture is distilled (a direct distillation method). Other methods include, for example, a method in which the β-mercapto carboxylic acids are extracted by adding an organic solvent such as ethyl acetate, toluene and the like to the reaction mixture, and the resultant is separated into an organic phase and an aqueous phase, and then the organic phase is distilled (an extraction/distillation method) and the like.

In the present invention, either of the methods may be employed regardless of the physical properties of the β-mercapto carboxylic acids. However, with the β-mercapto carboxylic acids which have high solubility in water, the direct distillation method is preferable, and with the β-mercapto carboxylic acids which can be extracted in an organic solvent, the extraction/distillation method is preferable.

When the reaction liquid containing the β-mercapto carboxylic acid is treated by the direct distillation method, a salt of the β-mercapto carboxylic acid may be formed in some cases because of reaction of the β-mercapto carboxylic acid with the hydroxide or oxide of an alkali metal or alkaline earth metal, or organic base, which is used as the pH adjuster.

When a salt of the β-mercapto carboxylic acid is formed, the amount of the acid recovered from distillation decreases. In order to avoid this, it is preferable to distill the reaction liquid after making the reaction liquid acidic by adding sulfuric acid, nitric acid, hydrochloric acid or the like in an amount from equivalent to a little excess of the amount of the pH adjuster used.

In addition, there are compounds with high crystallizability among the β-mercapto carboxylic acid and β-mercapto carboxylic acid amide synthesized from the α,β-unsaturated carboxylic acid or α,β-unsaturated carboxylic acid amide.

When the synthesized β-mercapto carboxylic acid and β-mercapto carboxylic acid amide have high crystallizability, these can be extracted with a solvent which has high affinity with the synthesized β-mercapto carboxylic acids, and the resultant can be crystallized, whereby the desired β-mercapto carboxylic acids are purified (isolated).

In the case of purification by distillation, the distillation apparatus used for distillation is not particularly limited, and there may be used known distillation apparatuses such as a batch distillation apparatus, a continuous distillation apparatus, a tower type distillation apparatus, and the like.

When distillation is carried out industrially in a large amount, it is preferable to use a continuous rectification apparatus composed of a heater, a rectification column, and a condenser, from the viewpoint of quality stabilization and productivity improvement and the like.

The recrystallization method can generally be applied when the desired β-mercapto carboxylic acids are compounds which are solids at ordinary temperature.

The recrystallization method may be any mode selected from poor solvent crystallization by addition of a poor solvent in which the β-mercapto carboxylic acids have low solubility, neutralization crystallization by addition of an acid or base, cooling crystallization by cooling of the reaction liquid, and the like.

By satisfying the conditions as described above, the β-mercapto carboxylic acids are produced in high productivity.

EXAMPLE

Hereinafter, the present invention will be described more specifically with reference to Examples, Comparative Examples, and Experimental Examples, but the present invention is not limited to these Examples.

In the following examples, "%" is based on mass unless otherwise noted.

Further, as for the reaction initiation time and reaction initiation pressure, the reaction time is at the time that the temperature of the reaction liquid reached a predetermined reaction temperature, and the pressure at this reaction initiation is described as the reaction initiation pressure.

In addition, the reaction time shows the time which elapsed since the reaction temperature reached a predetermined temperature.

Further, $H_2S$ equivalents/crotonic acid shows the number of equivalents of $H_2S$ fed relative to 1 equivalent of crotonic acid.

Further, base equivalents/crotonic acid indicates the number of equivalents of a base (the pH adjuster) added relative to 1 equivalent of crotonic acid.

In addition, "pH" was measured using the following pH meter.

pH instrument: Digital pH Controller Type FD-02, manufactured by Tokyo Glass Kikai Co., Ltd.

pH electrode: Electrode for pH Controller Type CE-108C, manufactured by Tokyo Glass Kikai Co., Ltd.

In the Examples, each component was measured by high performance liquid chromatography analysis (hereafter referred to as the "HPLC analysis"). The analytical conditions thereof are as follows:

Column: Shodex NN-814 (length, 20 cm; inner diameter, 0.5 cm; manufactured by Showa Denko K.K.);
Column Temperature: 40° C.;
Eluent: 0.1% $H_3PO_4$, 8 mM $KH_2PO_4$;
Flow Rate: 1.5 mL/min;
Detection: RI, UV (detection wavelength, 210 nm).

[Investigation of Solvent]

Example 1

To N, N-dimethylformamide (357 g, manufactured by Junsei Chemical Co., Ltd.) placed in a 500 ml autoclave made of Hastelloy C (a registered trademark), there were added crotonic acid (34.0 g, 0.40 mol; manufactured by Tokyo Chemical Ind. Co., Ltd.) and 4.7 g of a 10% aqueous solution of sodium hydroxide (a solution of solid sodium hydroxide dissolved in purified water, which is obtained by distilling ionic exchanged water) as a base to adjust the pH. The resultant was then stirred to produce a homogeneous solution.

While keeping the temperature of the solution in a range of 2 to 7° C., the solution was made to absorb hydrogen sulfide (26.9 g, 0.79 mol; $H_2S$ equivalents/crotonic acid, 2.0; manufactured by Sumitomo Seika Chemicals Co., Ltd.).

In addition, the pH electrode was immersed to the liquid after the absorption of hydrogen sulfide, and then the pH was measured at 6° C. and showed a value of 7.3.

Thereafter, the autoclave was closed tightly, the temperature was raised to 100° C., and the reaction was conducted for 5 hours.

After completion of the reaction, the reactor was cooled to 25° C. Then, a sample was taken from the solution in the autoclave, and analyzed by using HPLC to confirm the production of 3-mercaptobutanoic acid (40 g, 0.33 mol; yield, 84%). The conversion of crotonic acid was 99%.

Further, the reaction pressure was 0.5 MPa at the beginning of the reaction and 0.4 MPa at the end of the reaction. When the reactor was opened and the pH of the reaction liquid in which dissolved hydrogen sulfide was left was measured, the pH at 25° C. was 6.7.

Examples 2 to 5

Investigation was carried out without changing the amounts of the crotonic acid, the solvent and the hydrogen sulfide ($H_2S$ equivalents/crotonic acid), but with changing the kind of the solvent, and the reaction temperature.

Namely, reactions were carried out in the same manner as in Example 1 except that the kind of the solvent, the amount of the hydrogen sulfide ($H_2S$ equivalents/crotonic acid), and the reaction temperature were changed as listed in Table 1. The results are shown in Table 1.

Comparative Examples 1 to 4

Investigation was carried out without changing the amounts of the crotonic acid and the solvent but with changing in the kind of the solvent, the amount of the hydrogen sulfide ($H_2S$ equivalents/crotonic acid), and the reaction temperature.

Namely, reactions were carried out in the same manner as in Example 1 except that the kind of the solvent, the amount of the hydrogen sulfide ($H_2S$ equivalents/crotonic acid), and the reaction temperature were changed as listed in Table 1. The results are shown in Table 1.

TABLE 1

| | Solvent | | $H_2S$ Equivalents/ crotonic acid | Temperature (° C.) | Reaction time (hr) | Reaction pressure (MPa) (reaction initiation → end) | pH (before reaction → after reaction) | Conversion of Crotonic acid, (%) | 3-Mercapto-butanoic acid, yield (%) |
|---|---|---|---|---|---|---|---|---|---|
| | Kind | Mixing ratio | | | | | | | |
| Example 1 | DMF/ Water | DMF (98.83 w/w %), Water (1.17 w/w %) | 2 | 100 | 5 | 0.7→0.5 | 5.8→5.5 | 100% | 82% |
| Example 2 | NMP/ Water | NMP (98.83 w/w %), Water (1.17 w/w %) | 2 | 100 | 5 | 0.7→0.5 | 5.9→5.5 | 100% | 82% |
| Example 3 | NMP/ Water | NMP (79.06 w/w %), Water (20.94 w/w %) | 2 | 130 | 5 | 0.8→0.5 | 6.9→6.3 | 100% | 81% |
| Example 4 | DMA/ Water | DMA (98.83 w/w %), Water (1.17 w/w %) | 2 | 100 | 5 | 0.7→0.5 | 7.0→6.6 | 100% | 80% |
| Example 5 | DMI/ Water | DMI P (98.83 w/w %), Water (1.17 w/w %) | 2 | 100 | 5 | 0.7→0.5 | 7.1→6.7 | 100% | 81% |
| Comparative Example 1 | Acetone/ Water | Acetone (98.83 w/w %), Water (1.17 w/w %) | 2.4 | 100 | 5 | 1.1→1.0 | 5.4→5.2 | 29% | 5% |
| Comparative Example 2 | Ethyl acetate/ Water | Ethyl acetate (98.83 w/w %), Water (1.17 w/w %) | 2 | 130 | 5 | 1.0→1.0 | 5.0→4.8 | 21% | 8% |

TABLE 1-continued

|  | Solvent | | $H_2S$ Equivalents/ crotonic acid | Temperature (°C.) | Reaction time (hr) | Reaction pressure (MPa) (reaction initiation → end) | pH (before reaction → after reaction) | Conversion of Crotonic acid, (%) | 3-Mercapto-butanoic acid, yield (%) |
|---|---|---|---|---|---|---|---|---|---|
|  | Kind | Mixing ratio |  |  |  |  |  |  |  |
| Comparative Example 3 | Hexane/ Water | Hexane (98.83 w/w %), Water (1.17 w/w %) | 2 | 130 | 5 | 1.1→1.1 | 8.1→8.0 | 5% | 3% |
| Comparative Example 4 | Toluene/ Water | Toluene (98.83 w/w %), Water (1.17 w/w %) | 2 | 130 | 5 | 0.6→0.6 | 8.1→8.1 | 2% | 1% |

DMF: N,N-dimethylformamide
NMP: N-methylpyrrolidone
DMA: N,N-dimethylacetamide
DMI: N,N-dimethylimidazolidinone

[Investigation of Base (pH Adjuster)]

Example 6

To N-methylpyrrolidone (303 g, manufactured by Junsei Chemical Co., Ltd.) and purified water (54 g) placed in a 500 mL autoclave made of Hastelloy C (a registered trademark), there were added crotonic acid (34.0 g, 0.40 mole) and 4.7 g of a 10% aqueous solution of sodium hydroxide (a solution of solid sodium hydroxide dissolved in purified water) as a base to adjust the pH. The resultant was then stirred at room temperature to produce a homogeneous solution. The content of water in the solvent was 16.1%.

While keeping the temperature of the solution in a range of 2 to 7° C., the solution was made to absorb hydrogen sulfide (26.9 g, 0.79 mol; $H_2S$ equivalents/crotonic acid, 2.0; manufactured by Sumitomo Seika Chemicals Co., Ltd.).

In addition, the pH electrode was immersed to the liquid after the absorption of hydrogen sulfide, and then the pH was measured at 6° C. and showed a value of 7.3.

Thereafter, the autoclave was closed tightly, the temperature was raised to 100° C., and the reaction was conducted for 5 hours.

After completion of the reaction, the reactor was cooled to 25° C. Then, a sample was taken from the solution in the autoclave, and analyzed by using HPLC to confirm the production of 3-mercaptobutanoic acid (39 g, 0.33 mol; yield, 82%). The conversion of crotonic acid was 97%.

Further, the reaction pressure was 0.5 MPa at the beginning of the reaction and 0.4 MPa at the end of the reaction. When the reactor was opened and the pH of the reaction liquid in which dissolved hydrogen sulfide was left was measured, the pH at 25° C. was 6.7.

Examples 7 to 15

Investigation was carried out without changing the amounts of the crotonic acid and the solvent but with changing the kind of the base (pH adjuster) and the base equivalents/crotonic acid.

Namely, reactions were carried out in the same manner as in Example 6 except that the kind of the base (pH adjuster) and the amount of the base (base equivalents/crotonic acid) were changed as listed in Table 2. The results are shown in Table 2.

TABLE 2

|  | Solvent | Base | Base equivalents/ crotonic acid | $H_2S$ equivalents/ crotonic acid | Reaction pressure (MPa) (reaction initiation → end) | pH (before reaction → after reaction) | Conversion of Crotonic acid, (%) | 3-Mercapto-butanoic acid, yield (%) |
|---|---|---|---|---|---|---|---|---|
| Example 6 | NMP/Water | NaOH | 0.03 | 2 | 0.5→0.4 | 7.3→6.7 | 97% | 82% |
| Example 7 | NMP/Water | KOH | 0.03 | 2 | 0.6→0.4 | 7.0→6.4 | 99% | 78% |
| Example 8 | NMP/Water | $Ca(OH)_2$ | 0.03 | 2 | 0.6→0.4 | 7.4→6.8 | 100% | 82% |
| Example 9 | NMP/Water | LiOH | 0.03 | 2 | 0.6→0.3 | 7.0→6.4 | 100% | 79% |
| Example 10 | NMP/Water | NaOH | 0.10 | 2 | 0.5→0.4 | 7.8→7.1 | 100% | 83% |
| Example 11 | DMF/Water | — | — | 2 | 0.9→0.5 | 5.8→5.5 | 92% | 76% |
| Example 12 | NMP/Water | $Et_2NH$ | 0.03 | 2 | 0.6→0.4 | 7.2→6.7 | 100% | 82% |
| Example 13 | NMP/Water | $Et_3N$ | 0.03 | 2 | 0.6→0.4 | 7.2→6.5 | 100% | 81% |
| Example 14 | NMP/Water | Pyridine | 0.03 | 2 | 0.6→0.4 | 7.0→6.5 | 100% | 79% |
| Example 15 | NMP/Water | — | — | 2 | 0.9→0.5 | 5.9→5.5 | 72% | 61% |

[Investigation of pH]

Examples 16 to 18, Experimental Examples 1 to 3

Investigation was carried out without changing the amounts of the crotonic acid and the solvent but with changing the amount of the base.

Namely, reactions were carried out in the same manner as in Example 6 except that the amount of the base (base equivalents/crotonic acid) was changed as listed in Table 3. The results are shown in Table 3.

ide (a solution of solid sodium hydroxide in purified water). The resultant was then stirred at room temperature to produce a homogeneous solution.

While keeping the temperature of the solution in a range of 2 to 7° C., the solution was made to absorb hydrogen sulfide (48 g, 1.4 mol; $H_2S$ equivalents/crotonic acid; manufactured by Sumitomo Seika Chemicals Co., Ltd.).

In addition, the pH electrode was immersed to the liquid after the absorption of hydrogen sulfide, and then the pH was measured at 6° C. and showed a value of 7.3.

TABLE 3

| | Solvent | Base | Base equivalents/ crotonic acid | $H_2S$ equivalents/ crotonic acid | Reaction pressure (MPa) (reaction initiation → end) | pH (before reaction → after reaction) | Conversion of Crotonic acid, (%) | 3-Mercapto-butanoic acid, yield (%) |
|---|---|---|---|---|---|---|---|---|
| Example 16 | NMP/Water | NaOH | 0.03 | 2 | 0.5→0.4 | 7.3→6.7 | 97% | 82% |
| Example 17 | NMP/Water | NaOH | 0.10 | 2 | 0.5→0.4 | 7.7→7.1 | 100% | 83% |
| Example 18 | NMP/Water | NaOH | 0.50 | 2 | 0.4→0.3 | 8.4→7.8 | 100% | 83% |
| Experimental Example 1 | NMP/Water | — | — | 2 | 0.9→0.5 | 6.0→5.5 | 72% | 61% |
| Experimental Example 2 | NMP/Water | NaOH | 1.2 | 2 | 0.4→0.3 | 10.0→9.4 | 100% | 43% |
| Experimental Example 3 | NMP/Water | NaSH | 2.1 | 2 | 0.3→0.3 | 13.0→12.9 | 100% | 31% |

[Investigation of Concentration of Crotonic Acid (α,β-Unsaturated Carboxylic Acids)]

Examples 19 to 21

Investigation was carried out without changing the amount of the solvent but with changing the amount of the crotonic acid as listed in Table 4. In addition, the investigation was conducted without changing the amount of the base (base equivalents/crotonic acid) and the amount of the hydrogen sulfide ($H_2S$ equivalents/crotonic acid).

Namely, reactions were conducted in the same manner as in Example 6 except that the amount of the crotonic acid was changed as listed in Table 4. The results are shown in Table 4.

Thereafter, the autoclave was closed tightly, the temperature was raised to 70° C., and the reaction was conducted for 4 hours.

After completion of the reaction, the reactor was cooled to 25° C. Then, a sample was taken from the solution in the autoclave, and analyzed by using HPLC to confirm the production of 3-mercaptobutanoic acid (48.6 g, 0.40 mol; yield, 59%). The conversion of crotonic acid was 65%.

In addition, the reaction pressure was 1.2 MPa at the beginning of the reaction and 0.8 MPa at the end of the reaction. When the reactor was opened and the pH of the reaction liquid in which dissolved hydrogen sulfide was left was measured, the pH at 25° C. was 6.8.

TABLE 4

| | Concentration of Crotonic acid | Solvent | Base | Base equivalents/ crotonic acid | $H_2S$ equivalents/ crotonic acid | Reaction pressure (MPa) (reaction initiation → end) | pH (before reaction → after reaction) | Conversion of Crotonic acid (%) | 3-Mercapto-butanoic acid, yield (%) |
|---|---|---|---|---|---|---|---|---|---|
| Example 19 | 8% | NMP/Water | NaOH | 0.03 | 2 | 0.5→0.4 | 7.3→6.7 | 97% | 83% |
| Example 20 | 15% | NMP/Water | NaOH | 0.03 | 2 | 1.5→1.1 | 7.3→6.6 | 97% | 86% |
| Example 21 | 20% | NMP/Water | NaOH | 0.03 | 2 | 2.3→1.5 | 7.5→6.7 | 93% | 80% |

* The concentration of crotonic acid is described as a proportion of crotonic acid in the weight of all raw materials.

[Investigation of Temperature]

Example 22

To N-methylpyrrolidone (242 g) and purified water (44 g) placed in a 500 mL autoclave made of Hastelloy C (a registered trademark), there were added crotonic acid (59 g, 0.69 mol) and 8.5 g of a 10% aqueous solution of sodium hydrox- Examples 23 and 24

Investigation was carried out without changing the amount of crotonic acid and the solvent but with a change only in the reaction temperature.

Namely, reactions were carried out in the same manner as in Example 22 except that the reaction temperature was changed as described in Table 5. The results are shown in Table 5.

TABLE 5

|  | Temperature (° C.) | Solvent | Base | Base equivalents/ crotonic acid | $H_2S$ equivalents/ crotonic acid | Reaction pressure (MPa) (reaction initiation → end) | pH (before reaction → after reaction) | Conversion Crotonic acid (%) | 3-Mercapto- butanoic acid, yield (%) |
|---|---|---|---|---|---|---|---|---|---|
| Example 22 | 70 | NMP/ Water | NaOH | 0.03 | 2 | 1.2→0.8 | 7.3→6.8 | 65% | 59% |
| Example 23 | 100 | NMP/ Water | NaOH | 0.03 | 2 | 1.5→1.1 | 7.3→6.6 | 97% | 86% |
| Example 24 | 130 | NMP/ Water | NaOH | 0.03 | 2 | 1.9→1.4 | 7.3→6.7 | 100% | 87% |

[Investigation of $H_2S$ Equivalents/Crotonic Acid (Number of Equivalents of Hydrogen Sulfide Relative to 1 Equivalent of Crotonic Acid)]

Example 25

To N-methylpyrrolidone (357 g) and purified water (55.1 g) placed in a 500 ml autoclave made of Hastelloy C (a registered trademark), there were added crotonic acid (5.7 g, 0.066 mol) and 0.3 g of a 10% aqueous solution of sodium hydroxide (a solution of solid sodium hydroxide dissolved in purified water). The resultant was then stirred at room temperature to produce a homogeneous solution.

While keeping the temperature of the solution in a range of 2 to 7° C., the solution was made to absorb hydrogen sulfide (4.5 g, 0.13 mol; $H_2S$ equivalents/crotonic acid, 2.0; manufactured by Sumitomo Seika Chemicals Co., Ltd.).

In addition, the pH electrode was immersed to the liquid after the absorption of hydrogen sulfide, and then the pH was measured at 6° C. and showed a value of 7.2.

Thereafter, the autoclave was closed tightly, the temperature was raised to 130° C., and the reaction was conducted for 4 hours.

After completion of the reaction, the reactor was cooled to 25° C. Then, a sample was taken from the solution in the autoclave, and analyzed by using HPLC to confirm the production of 3-mercaptobutanoic acid (6.0 g, 0.050 mol; yield, 75%). The conversion of crotonic acid was 80%.

In addition, the reaction pressure was 0.13 MPa at the beginning of the reaction and 0.06 MPa at the end of the reaction. When the reactor was opened and the pH of the reaction liquid in which dissolved hydrogen sulfide was left was measured, the pH at 25° C. was 7.1.

Examples 26 and 27

Investigation was carried out without changing the amount of the crotonic acid and the solvent but with changing only the amount of the hydrogen sulfide ($H_2S$ equivalents/crotonic acid).

Namely, reactions were conducted in the same manner as in Example 25 except that the amount of the hydrogen sulfide ($H_2S$ equivalents/crotonic acid) was changed as listed in Table 6. The results are shown in Table 6.

TABLE 6

|  | $H_2S$ equivalents/ Crotonic acid | Solvent | Base | Base equivalents/ crotonic acid | Reaction pressure (MPa) (reaction initiation → end) | pH (before reaction → after reaction) | Conversion of Crotonic acid (%) | 3-Mercapto- butanoic acid, yield (%) |
|---|---|---|---|---|---|---|---|---|
| Example 25 | 2 | NMP/ Water | NaOH | 0.03 | 0.13→0.06 | 7.2→7.1 | 80% | 75% |
| Example 26 | 4 | NMP/ Water | NaOH | 0.03 | 0.20→0.16 | 7.5→7.3 | 91% | 87% |
| Example 27 | 10 | NMP/ Water | NaOH | 0.03 | 0.54→0.51 | 7.5→7.2 | 100% | 98% |

INDUSTRIAL APPLICABILITY

According to the method of the present invention, the β-mercapto carboxylic acids are produced in high purity. The β-mercapto carboxylic acids obtained by the method of the present invention are useful as additives for polymer compounds, raw materials for producing other reactive compounds, and the like.

The invention claimed is:

1. A method for producing β-mercapto carboxylic acids, comprising:
    preparing a liquid consisting of hydrogen sulfide, a solvent, and any one of α,β-unsaturated carboxylic acids selected from an α,β-unsaturated carboxylic acid, an α,β-unsaturated carboxylic acid ester, an α,β-unsaturated amide, an α,β-unsaturated aldehyde, and an α,β-unsaturated ketone,
    or a liquid consisting of hydrogen sulfide, a solvent, a pH adjuster, and any one of α,β-unsaturated carboxylic acids selected from an α,β-unsaturated carboxylic acid, an α,β-unsaturated carboxylic acid ester, an α,β-unsaturated amide, an α,β-unsaturated aldehyde, and an α,β-unsaturated ketone; and then
    heating the liquid in a range of 70 to 200° C. to react the any one of the α,β-unsaturated carboxylic acids with the hydrogen sulfide, thereby producing any one of β-mercapto carboxylic acids which is selected from β-mercapto carboxylic acid, β-mercapto carboxylic acid ester, β-mercapto amide, β-mercapto aldehyde, and β-mercapto ketone, and corresponds to the α,β-unsaturated carboxylic acids used, wherein the liquid has a pH measured at 6° C. before the any one of the α,β-unsaturated carboxylic acids is reacted with the hydrogen sulfide in the range of 6.0 to 8.5, the pH adjuster is selected from a mineral acid, a lower carboxylic acid, a basic material containing an alkali metal or an alkaline earth metal, and an organic basic material selected from ammonia, ethylamine, propylamine, dimethylamine, diethylamine, diisopropylamine, dipropylamine, trimethylamine, triethylamine, pyridine, and morpholine, and the solvent is selected from a compound represented by the formula (1), and a mixed solvent comprising the compound represented by the formula (1) and water;

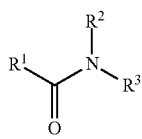
(1)

wherein $R^1$ represents any one of a hydrogen atom, an alkoxy group having 1 to 5 carbon atoms, an alkyl group having 1 to 5 carbon atoms, an amino group, and an alkylamino group having 1 to 5 carbon atoms; $R^2$ and $R^3$ each represents independently any of a hydrogen atom and an alkyl group having 1 to 5 carbon atoms; when both $R^2$ and $R^3$ are not a hydrogen atom, $R^2$ and $R^3$ may together form a ring structure through an alkylene group; further when both $R^1$ and $R^2$ are not a hydrogen atom, $R^1$ and $R^2$ may form a ring structure through an alkylene group.

2. The method for producing β-mercapto carboxylic acids according to claim 1, wherein the reaction is carried out at the range of 90 to 150° C.

3. The method for producing β-mercapto carboxylic acids according to claim 1, wherein the amount of water contained in the mixed solvent is 1 to 50% by mass.

4. The method for producing β-mercapto carboxylic acids according to claim 1, wherein the compound represented by the formula (1) is one or more kinds selected from N-methylformamide (MFA), N,N-dimethylformamide (DMF), N-ethylformamide (EFA), N,N-diethylformamide (DEF), N,N-dimethylacetamide (DMA), 1,3-dimethyl-2-imidazolidinone (DMI), and N-methyl-2-pyrrolidone (NMP).

5. The method for producing β-mercapto carboxylic acids according to claim 1, wherein the α,β-unsaturated carboxylic acids is an α,β-unsaturated carboxylic acid or an α,β-unsaturated carboxylic acid ester.

6. The method for producing β-mercapto carboxylic acids according to claim 1, wherein the α,β-unsaturated carboxylic acid is any one of acrylic acid, methacrylic acid, crotonic acid, 2-pentenoic acid, cinnamic acid, 2-methylcinnamic acid, 3-methycinnamic acid, 4-methylcinnamic acid, 2,3-dimethylcinnamic acid, 2,4-dimethylcinnamic acid, 3,4-dimethylcinnamic acid, 2-hydroxycinnamic acid, 3-hydroxycinnamic acid, 4-hydroxycinnamic acid, 2,3-dihydrocinnamic acid, 2,4-dihydrocinnamic acid, 3,4-dihydrocinnamic acid, 2-hexenoic acid, and 4-methyl-2-pentenoic acid.

7. The method for producing β-mercapto carboxylic acids according to claim 1, wherein the α,β-unsaturated carboxylic acid ester is any one of methyl acrylate, ethyl acrylate, propyl acrylate, butyl acrylate, methyl methacrylate, ethyl methacrylate, propyl methacrylate, butyl methacrylate, methyl crotonate, ethyl crotonate, propyl crotonate, butyl crotonate, methyl 2-pentenoate, ethyl 2-pentenoate, propyl 2-pentenoate, and butyl 2-pentenoate.

8. The method for producing β-mercapto carboxylic acids according to claim 1, wherein the α,β-unsaturated ketone is any one of cyclopentenone, cyclohexenone, and cycloheptenone.

9. The method for producing β-mercapto carboxylic acids according to claim 5, wherein the α,β-unsaturated carboxylic acid is any one of acrylic acid, methacrylic acid, crotonic acid, 2-pentenoic acid, cinnamic acid, 2-methylcinnamic acid, 3-methycinnamic acid, 4-methylcinnamic acid, 2,3-dimethylcinnamic acid, 2,4-dimethylcinnamic acid, 3,4-dimethylcinnamic acid, 2-hydroxycinnamic acid, 3-hydroxycinnamic acid, 4-hydroxycinnamic acid, 2,3-dihydrocinnamic acid, 2,4-dihydrocinnamic acid, 3,4-dihydrocinnamic acid, 2-hexenoic acid, and 4-methyl-2-pentenoic acid.

10. The method for producing β-mercapto carboxylic acids according to claim 5, wherein the α,β-unsaturated carboxylic acid ester is any one of methyl acrylate, ethyl acrylate, propyl acrylate, butyl acrylate, methyl methacrylate, ethyl methacrylate, propyl methacrylate, butyl methacrylate, methyl crotonate, ethyl crotonate, propyl crotonate, butyl crotonate, methyl 2-pentenoate, ethyl 2-pentenoate, propyl 2-pentenoate, and butyl 2-pentenoate.

* * * * *